United States Patent
Ohyama et al.

(10) Patent No.: US 7,667,592 B2
(45) Date of Patent: Feb. 23, 2010

(54) OPERATION SYSTEM AND METHOD OF NOTIFYING SYSTEM OPERATION INFORMATION OF SAME

(75) Inventors: Masahide Ohyama, Hachioji (JP); Hideyuki Shoji, Sagamihara (JP); Sumihiro Uchimura, Sagamihara (JP); Masanori Gocho, Hachioji (JP); Takashi Mihori, Akiruno (JP); Shinji Hatta, Hachioji (JP); Mitsumasa Okada, Hachioji (JP); Makoto Inaba, Kunitachi (JP); Masakazu Gotanda, Sagamihara (JP); Yoshitaka Honda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 336 days.

(21) Appl. No.: 11/811,798

(22) Filed: Jun. 12, 2007

(65) Prior Publication Data

US 2008/0129527 A1 Jun. 5, 2008

(30) Foreign Application Priority Data

Jun. 12, 2006 (JP) ............................. 2006-162918

(51) Int. Cl.
*G08B 1/08* (2006.01)
*G08B 13/14* (2006.01)
*A61B 1/04* (2006.01)

(52) U.S. Cl. .............................. 340/539.12; 340/572.1; 600/109; 600/118

(58) Field of Classification Search ................. 340/679, 340/568.1–572.9, 539.12; 600/101, 109–112, 600/118
See application file for complete search history.

(56) References Cited

U.S. PATENT DOCUMENTS

| | | | | |
|---|---|---|---|---|
| 7,256,696 B2* | 8/2007 | Levin | ....................... | 340/572.1 |
| 7,362,228 B2* | 4/2008 | Nycz et al. | ............... | 340/572.1 |
| 7,474,223 B2* | 1/2009 | Nycz et al. | ............... | 340/572.8 |
| 7,498,950 B1* | 3/2009 | Ertas et al. | ................... | 340/679 |
| 2002/0067263 A1* | 6/2002 | Tafoya et al. | ............ | 340/572.1 |
| 2003/0058097 A1* | 3/2003 | Saltzstein et al. | ........... | 340/531 |
| 2003/0097042 A1* | 5/2003 | Eino | ........................... | 600/118 |
| 2003/0174205 A1* | 9/2003 | Amling et al. | ................. | 348/65 |

FOREIGN PATENT DOCUMENTS

| | | |
|---|---|---|
| JP | 2003-070746 | 3/2003 |
| JP | 2003-076786 | 3/2003 |
| JP | 2005-065721 | 3/2005 |

* cited by examiner

*Primary Examiner*—Jennifer Mehmood
(74) *Attorney, Agent, or Firm*—Scully, Scott, Murphy & Presser, P.C.

(57) ABSTRACT

A treatment instrument output data analysis section includes a probe ID extraction section, an output waveform extraction section, a data analysis section and an analysis result output section. The analysis result output section of the treatment instrument output data analysis section can display on a centralized display panel a synthetic image made by synthesizing a frame image stored in an image storage section of an endoscopic camera apparatus and an analysis result analyzed by the data analysis section.

7 Claims, 13 Drawing Sheets

HANDLING TABLE

FIG.11

ELECTRODE ID: ID = 02 (MONOPOLAR ELECTRODE 2 = SNARE ELECTRODE)
OUTPUT WAVEFORM: PATTERN = 01
CONDITION: NOT DISCHARGED, BUT SQUEEZING SNARE OR BLEEDING FROM POLYP SCAR

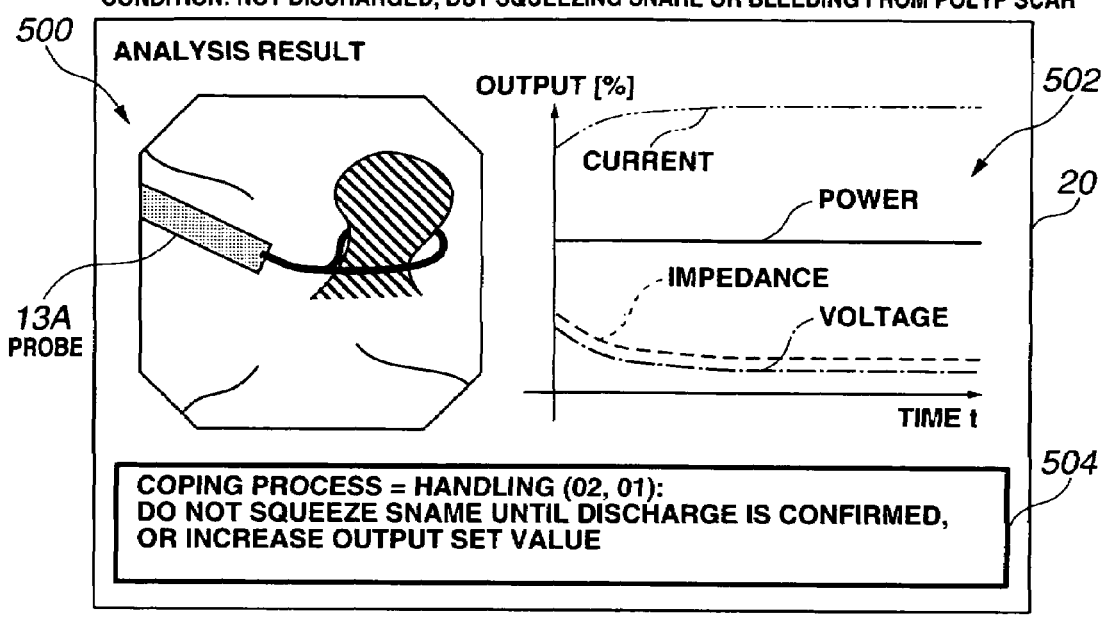

COPING PROCESS = HANDLING (02, 01):
DO NOT SQUEEZE SNAME UNTIL DISCHARGE IS CONFIRMED,
OR INCREASE OUTPUT SET VALUE

FIG.12

ELECTRODE ID: ID = 03 (MONOPOLAR ELECTRODE 3 = LOOP ELECTRODE)
OUTPUT WAVEFORM: PATTERN = 02
CONDITION: DISCHARGED AND BLEEDING IS STOPPED→BLEEDING AGAIN IF ELECTRODE IS MOVED

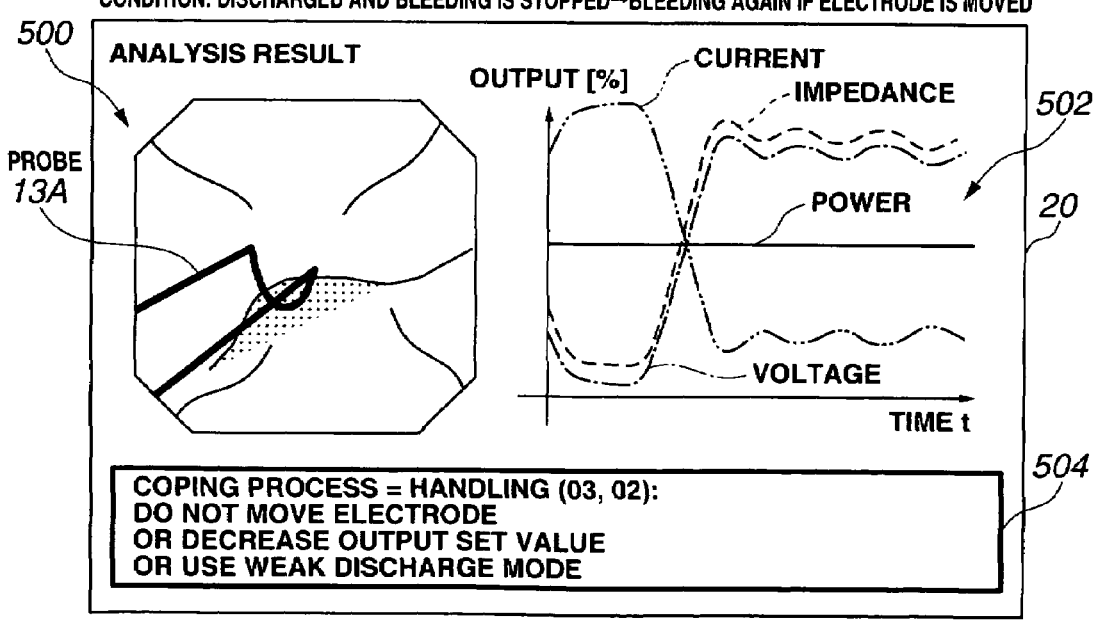

COPING PROCESS = HANDLING (03, 02):
DO NOT MOVE ELECTRODE
OR DECREASE OUTPUT SET VALUE
OR USE WEAK DISCHARGE MODE

ELECTRODE ID: ID = 11 (BIPOLAR ELECTRODE 1 = FORCEPS ELECTRODE)
OUTPUT WAVEFORM: PATTERN = 11
CONDITION: ELECTRODE IS LARGER THAN SET VALUE,
OR ELECTRODE IS SINKING IN SALINE/BLOOD

ELECTRODE ID: ID = 11 (BIPOLAR ELECTRODE 1 = FORCEPS ELECTRODE)
OUTPUT WAVEFORM: PATTERN = 12
CONDITION: NONCHARACTERISTIC

| EVALUATION PARAMETER | HIGH SKILL LEVEL | LOW SKILL LEVEL |
|---|---|---|
| NUMBER OF TIMES OF DESSECTION/TOTAL NUMBER OF TIMES OF OUTPUT (= DESSECTION TIME/TOTAL OUTPUT TIME) | SMALL | LARGE |
| AVERAGE DESSECTION TIME | LONG | SHORT |
| AVERAGE COAGULATION TIME | SHORT | LONG |
| DESSECTION TIME/OPERATION TIME | SMALL | LARGE |
| DESSECTION VOLUME/DESSECTION TIME | LARGE | SMALL |

OPERATION SYSTEM AND METHOD OF NOTIFYING SYSTEM OPERATION INFORMATION OF SAME

This application claims benefit of Japanese Application No. 2006-162918 filed on Jun. 12, 2006, the contents of which are incorporated by this reference.

BACKGROUND OF THE INVENTION

1. Field of the Invention

The present invention relates to an operation system for controlling multiple medical instruments and a method of notifying system operation information of the same.

2. Description of the Related Art

In recent years, an endoscopic operation system for performing a procedure by using an endoscope, for instance, has come into wide use as an operation system for performing the procedure by controlling multiple medical instruments, where a wide variety of medical instruments are used.

The medical instruments used for such an endoscopic operation system include an electric knife apparatus, an ultrasonic apparatus, an aeroperitoneum apparatus and the like in addition to an electronic endoscope system. These instruments are managed as a package system, and are controlled by an operating instrument placed under a system controller as proposed in Japanese Patent Laid-Open No. 2003-76786 or Japanese Patent Laid-Open No. 2003-70746 for instance.

On the other hand, Japanese Patent Laid-Open No. 2005-65721 discloses a medical information system as an operation system, wherein all information generated during an operation is recorded in order of generation thereof and displayed on a display unit so that the information can be complemented and exploited for a subsequent analysis and the like. The medical information system analyzes a process of the operation in detail after the operation, and obtains information on a surgical technique and improvement in the instruments. In particular, the system is intended to establish an optimal procedure for a target operation.

SUMMARY OF THE INVENTION

The present invention provides an operation system comprises: a treatment instrument used for a medical treatment apparatus for performing a treatment on an affected area; handling information storage means for storing handling information according to an operational status of the treatment instrument; operational status detection means for detecting the operational status of the treatment instrument; treatment instrument operational status recording means for recording the operational status of the treatment instrument detected by the operational status detection means; operational status analysis means for analyzing the operational status of the treatment instrument recorded by the treatment instrument operational status recording means; and handling information extraction means for extracting the handling information stored in the handling information storage means based on the operational status of the treatment instrument analyzed by the operational status analysis means.

The present invention provides a method of notifying system operation information of an operation system comprises: a treatment instrument identification information detecting step of detecting identification information for identifying a type of a treatment instrument used for a medical treatment apparatus for performing a treatment on an affected area; an operational status detection step of detecting operational status information of the treatment instrument; a treatment instrument operational status recording step of recording the operational status information of the treatment instrument detected by the operational status detection step; an operational status analysis step of analyzing the operational status information of the treatment instrument recorded by the treatment instrument operational status recording step based on the identification information detected by the treatment instrument identification information detecting step; a handling information extraction step of extracting the handling information based on the operational status information of the treatment instrument analyzed by the operational status analysis step from the handling information storage means for storing the handling information according to the operational status information of each type of the treatment instrument; and an operational status notifying step of outputting the operational status information analyzed by the operational status analysis step to notification means based on a predetermined notification condition.

BRIEF DESCRIPTION OF THE DRAWINGS

FIG. 11 is a fifth drawing describing the processing of FIG. 6;

FIG. 12 is a sixth drawing describing the processing of FIG. 6;

DETAILED DESCRIPTION OF THE PREFERRED EMBODIMENTS

Hereunder, embodiments of the present invention will be described with reference to the drawings.

First Embodiment

Figure 1:
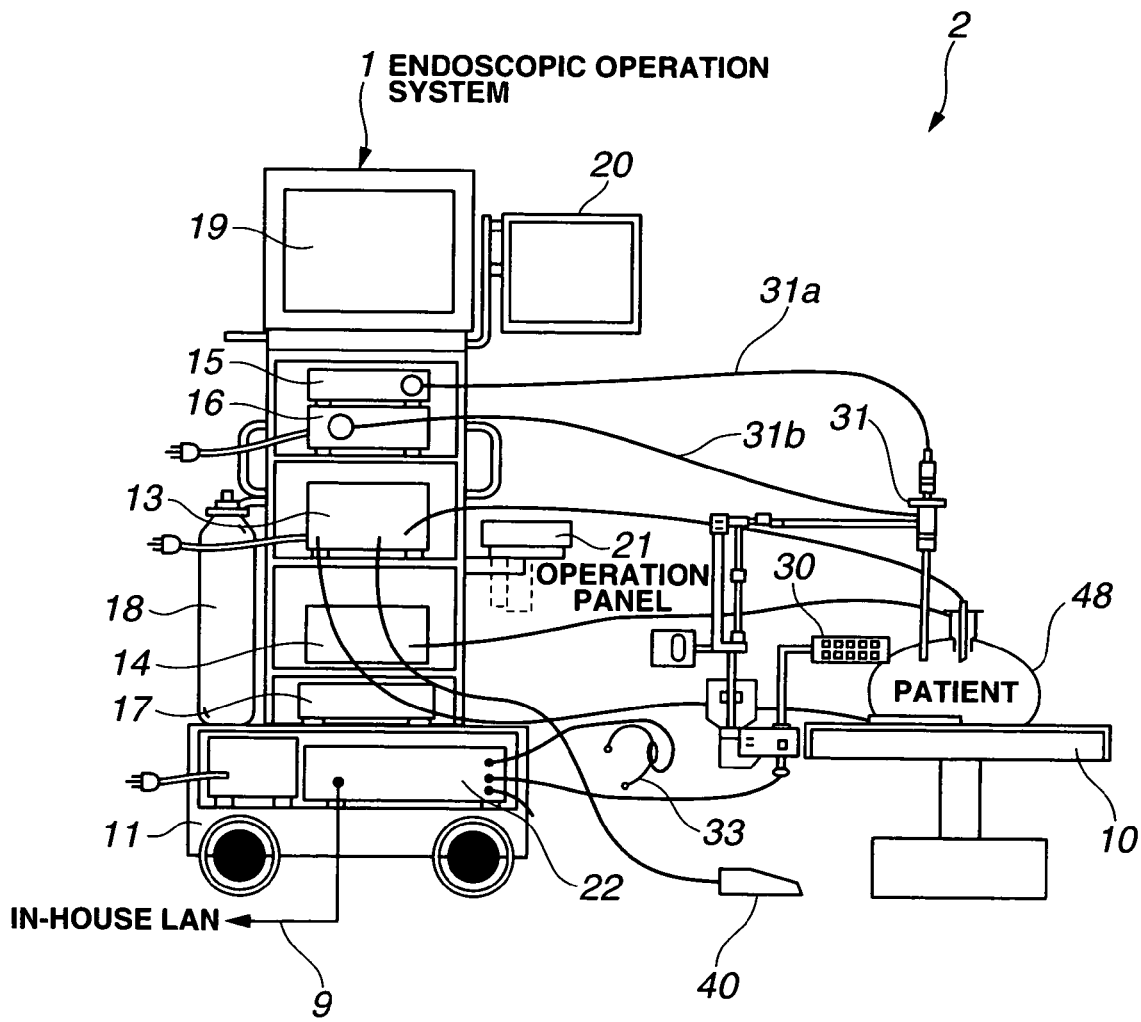
FIG. 1 is a block diagram showing a configuration of an endoscopic operation system according to a first embodiment of the present invention.
Figure 2:
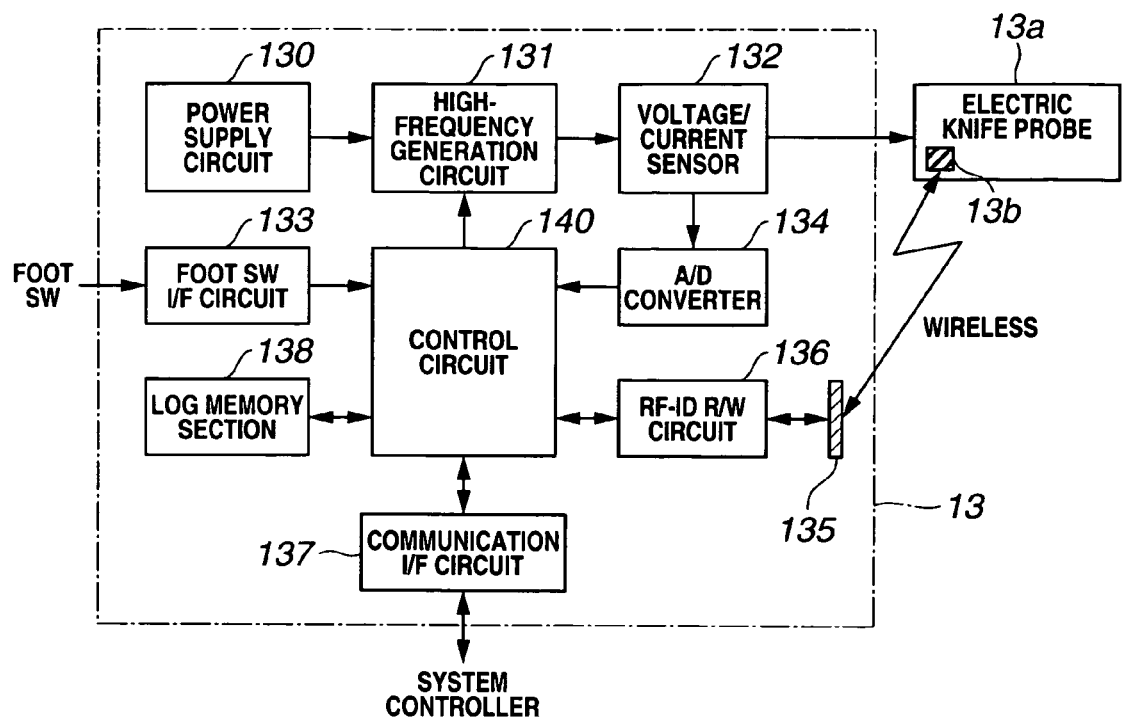
FIG. 2 is a block diagram showing the configuration of an electric knife apparatus of FIG. 1.
Figure 3:
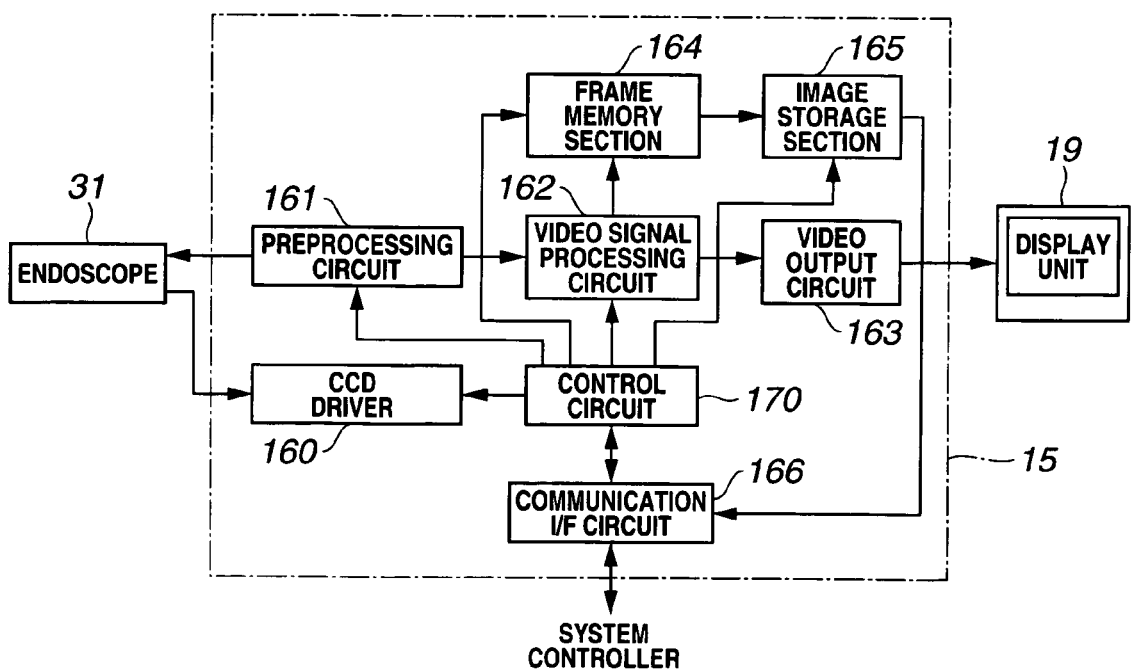
FIG. 3 is a block diagram showing the configuration of an endoscopic camera apparatus of FIG. 1.
Figure 4:
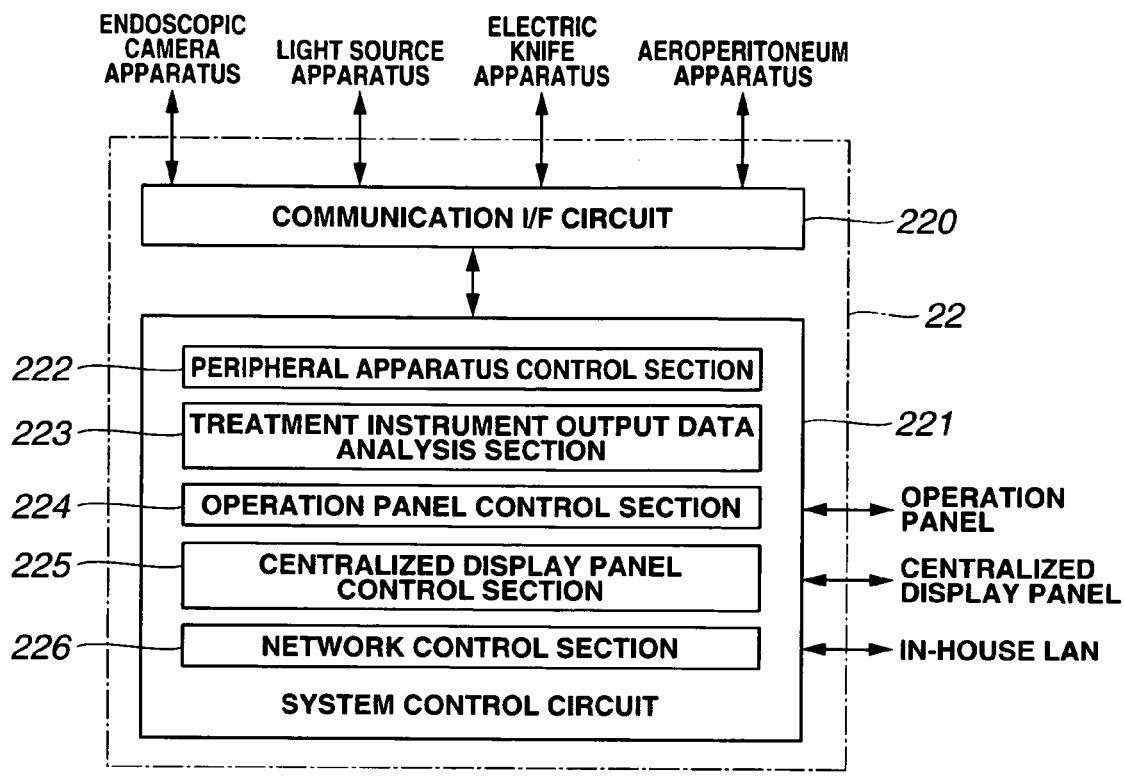
FIG. 4 is a block diagram showing the configuration of a system controller of FIG. 1.
Figure 5:
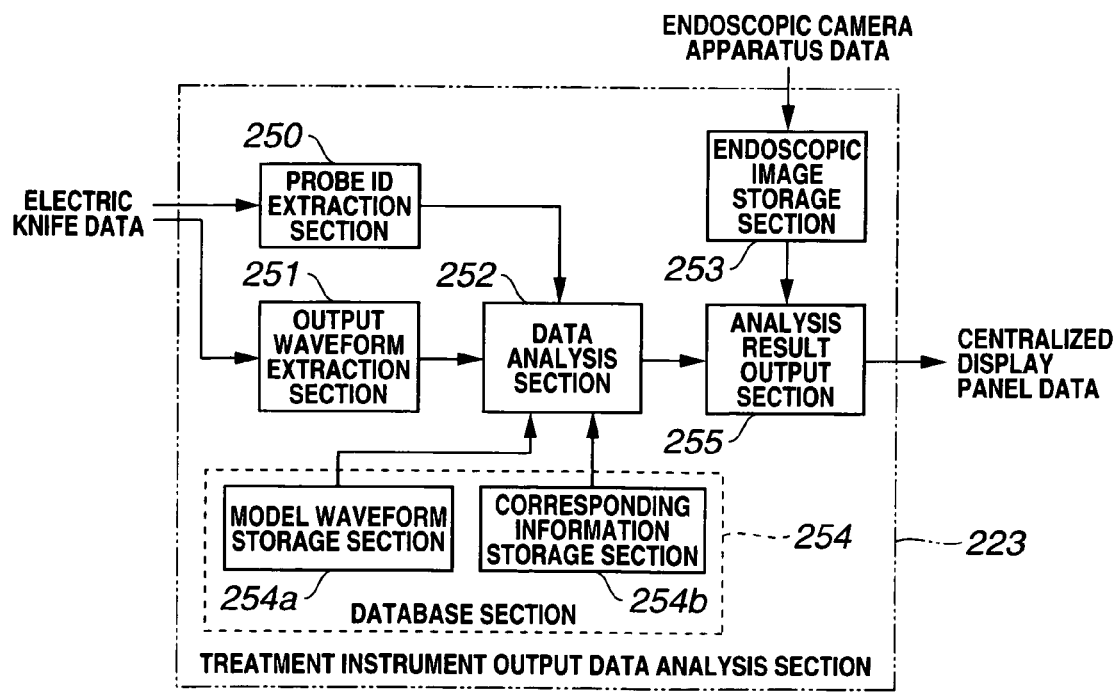
FIG. 5 is a block diagram showing the configuration of a treatment instrument output data analysis section of FIG. 4.
Figure 6:
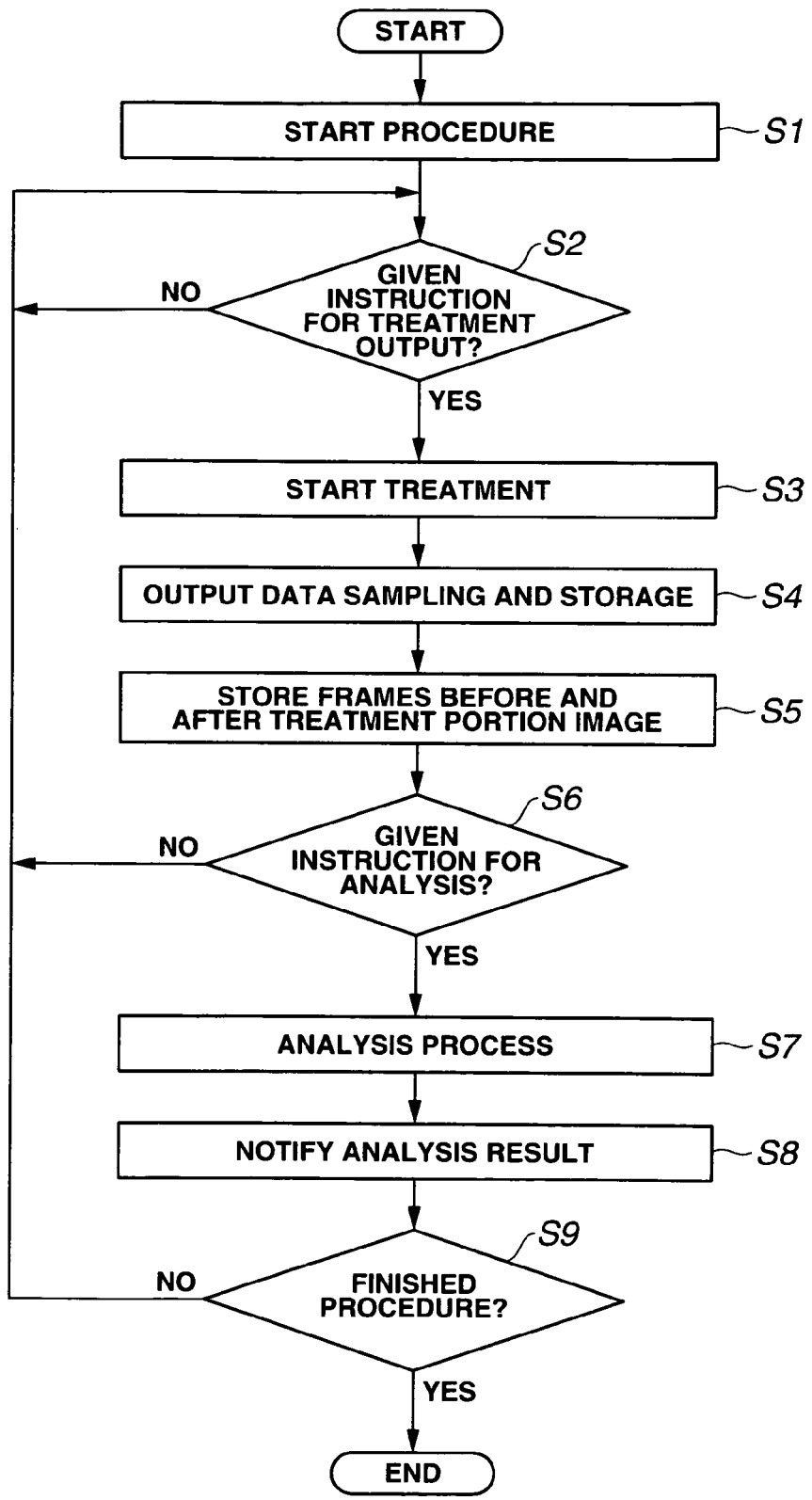
FIG. 6 is a flowchart describing processing of the endoscopic operation system of FIG. 1.
Figure 7:
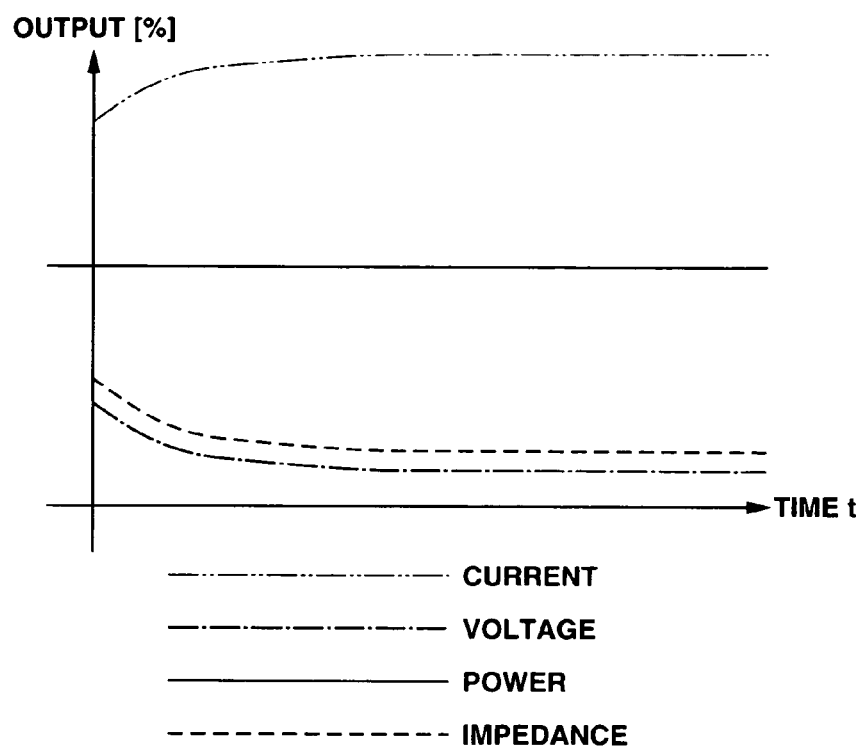
FIG. 7 is a first drawing describing the processing of FIG. 6.
Figure 8:
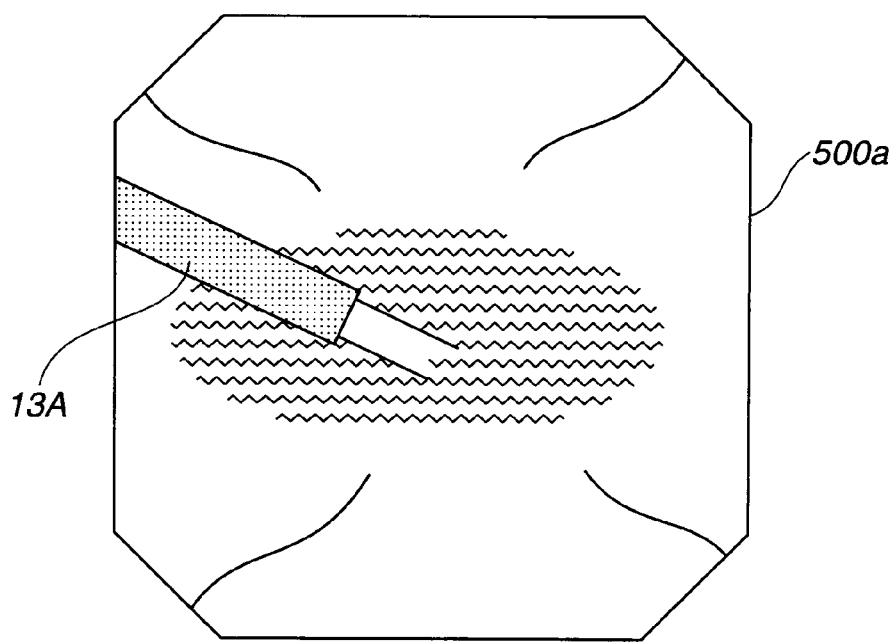
FIG. 8 is a second drawing describing the processing of FIG. 6.
Figure 9:
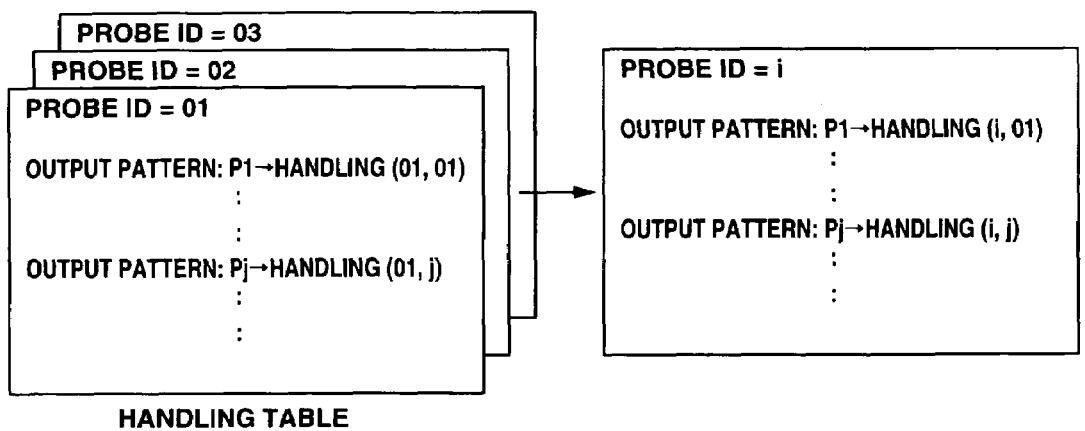
FIG. 9 is a third drawing describing the processing of FIG. 6.
Figure 10:
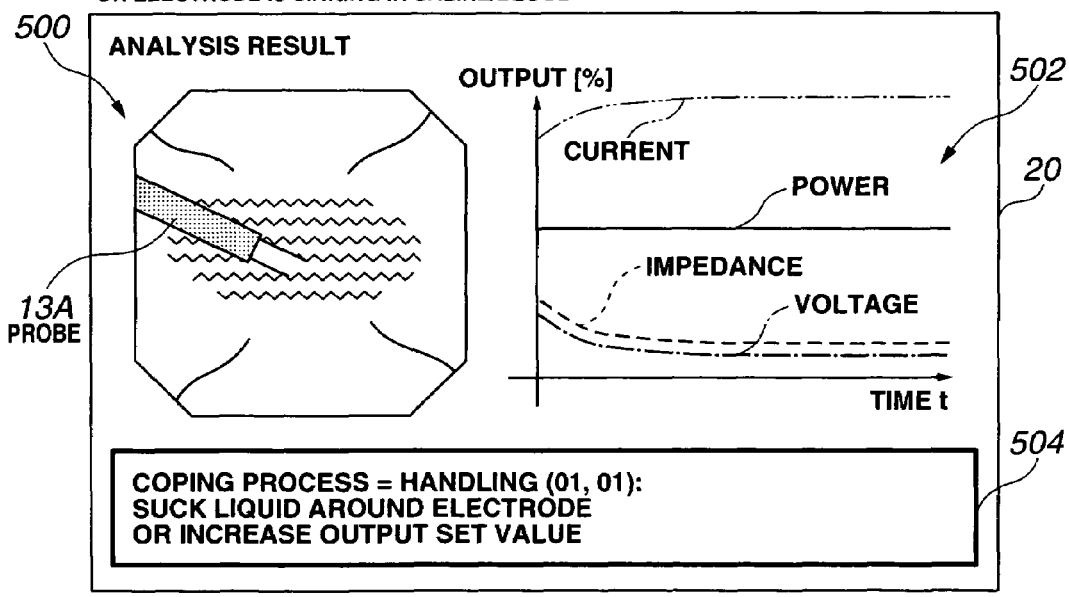
FIG. 10 is a fourth drawing describing the processing of FIG. 6.
Figure 13:
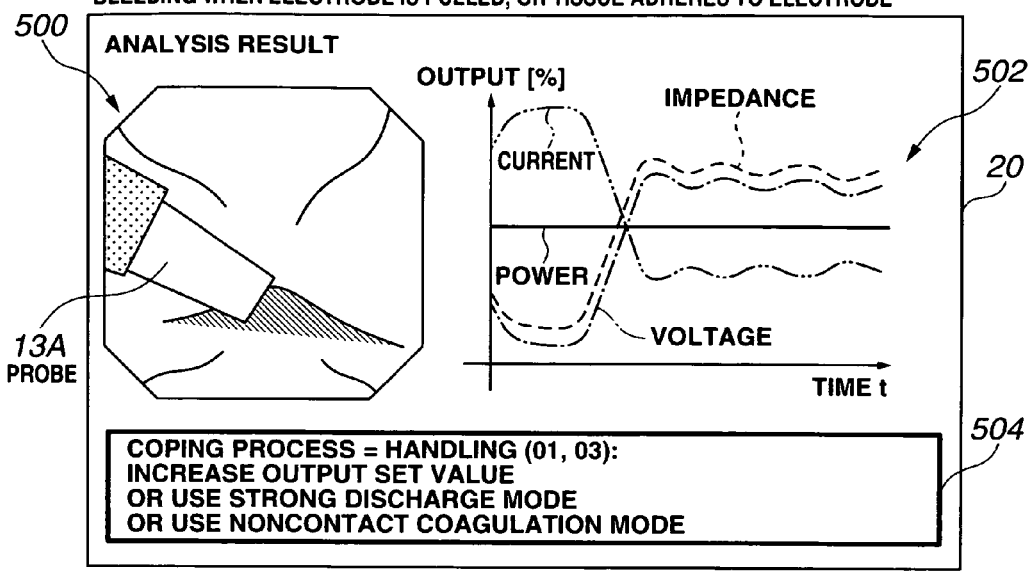
FIG. 13 is a seventh drawing describing the processing of FIG. 6.
Figure 14:
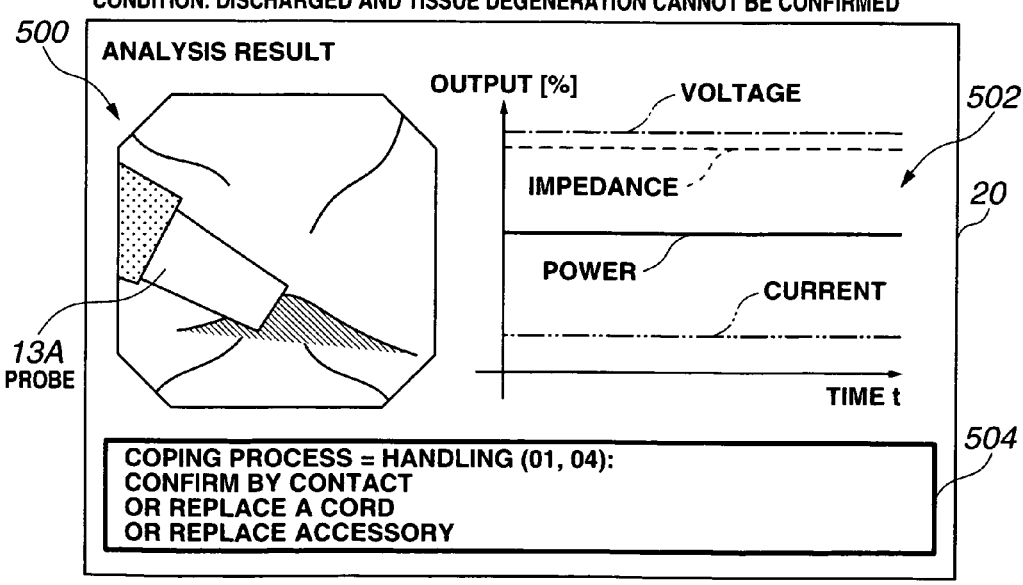
FIG. 14 is an eighth drawing describing the processing of FIG. 6.
Figure 15:
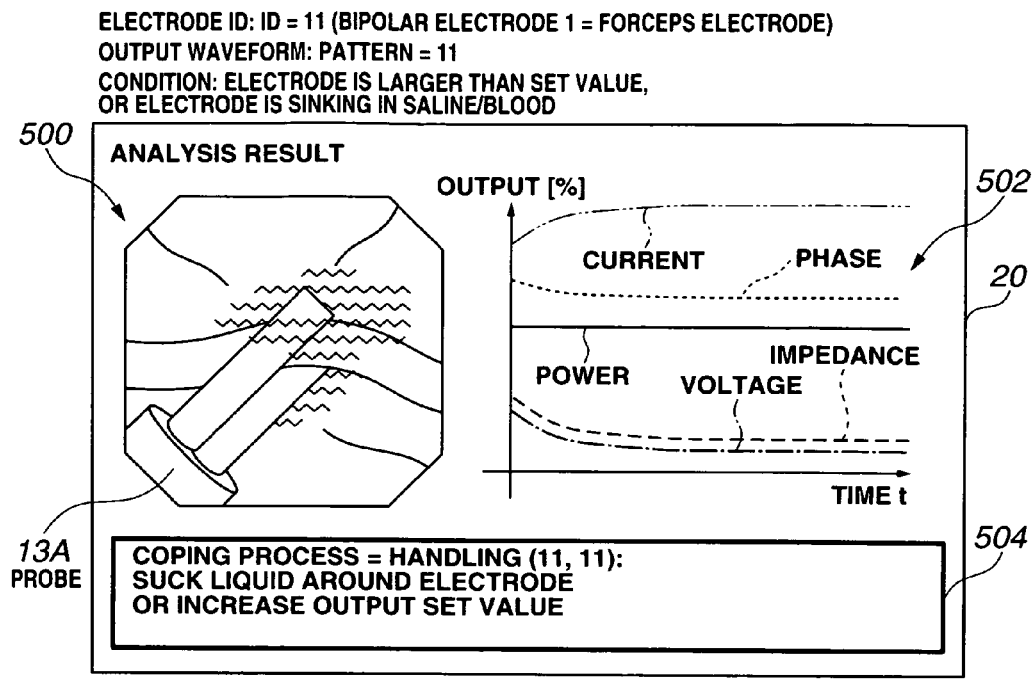
FIG. 15 is a ninth drawing describing the processing of FIG. 6.
Figure 16:
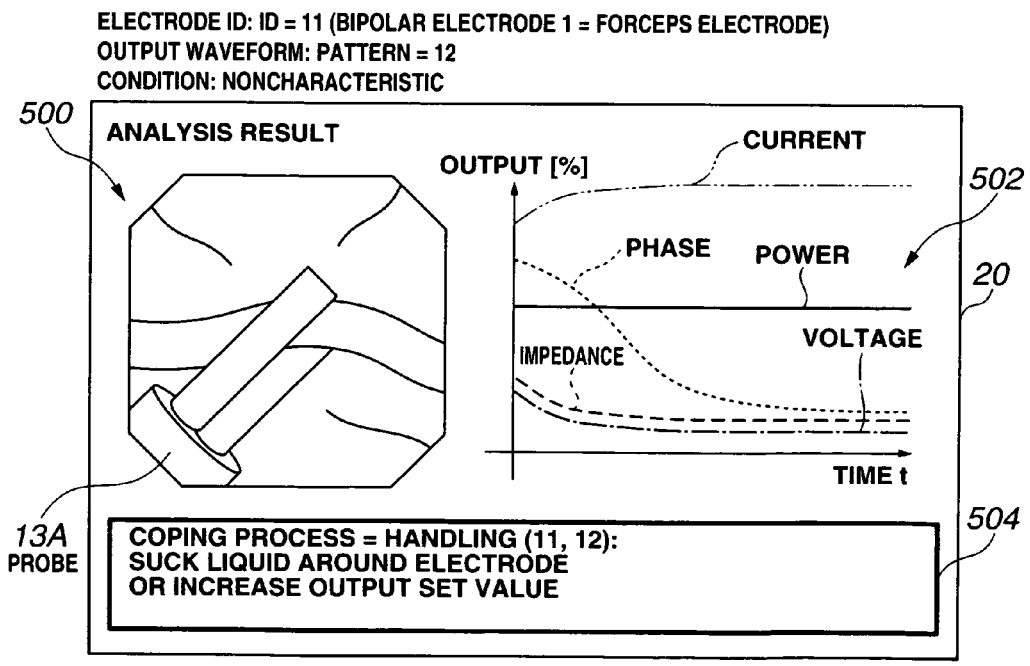
FIG. 16 is a tenth drawing describing the processing of FIG. 6.
Figure 17:
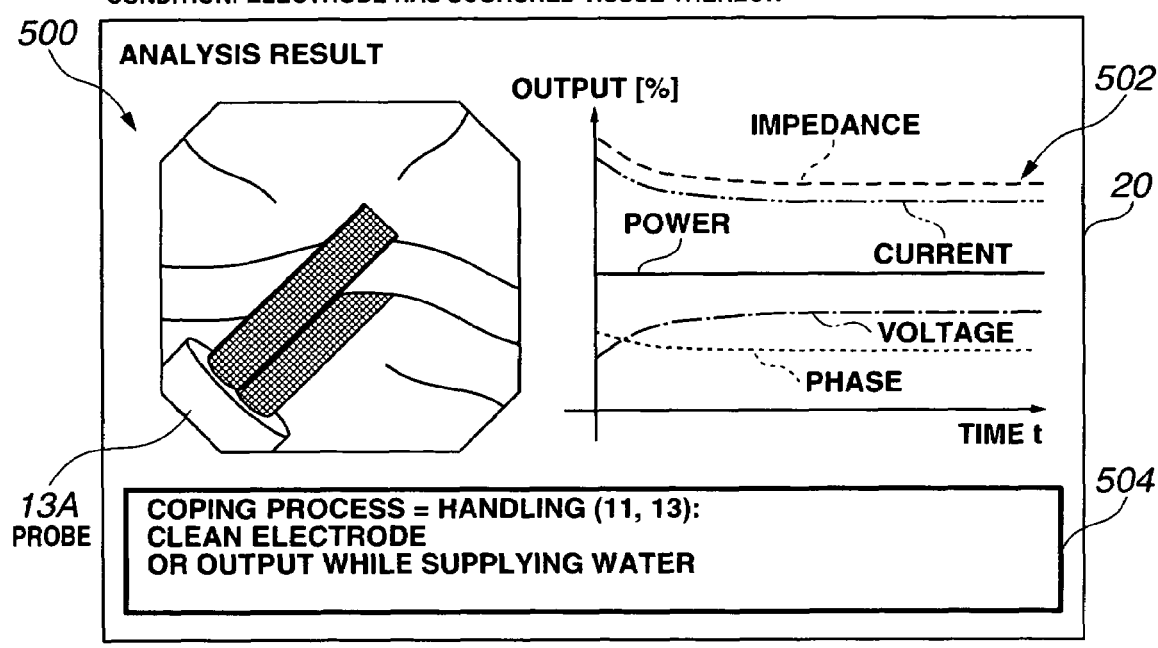
FIG. 17 is an eleventh drawing describing the processing of FIG. 6.

FIGS. 1 to 17 relate to a first embodiment of the present invention. FIG. 1 is a block diagram showing a configuration of an endoscopic operation system. FIG. 2 is a block diagram showing the configuration of an electric knife apparatus of FIG. 1. FIG. 3 is a block diagram showing the configuration of an endoscopic camera apparatus of FIG. 1. FIG. 4 is a block diagram showing the configuration of a system controller of FIG. 1. FIG. 5 is a block diagram showing the configuration of a treatment instrument output data analysis section of FIG. 4. FIG. 6 is a flowchart describing processing of the endoscopic operation system of FIG. 1. FIG. 7 is a first drawing describing the processing of FIG. 6. FIG. 8 is a second drawing describing the processing of FIG. 6. FIG. 9 is a third drawing describing the processing of FIG. 6. FIG. 10 is a fourth drawing describing the processing of FIG. 6. FIG. 11 is a fifth drawing describing the processing of FIG. 6. FIG. 12 is a sixth drawing describing the processing of FIG. 6. FIG. 13 is a seventh drawing describing the processing of FIG. 6. FIG. 14 is an eighth drawing describing the processing of FIG. 6. FIG. 15 is a ninth drawing describing the processing of FIG. 6. FIG. 16 is a tenth drawing describing the processing of FIG. 6. And FIG. 17 is an eleventh drawing describing the processing of FIG. 6.

First, a description will be given by using FIG. 1 as to the overall configuration of an endoscopic operation system 1 as the operation system of the present embodiment, which is placed in an operation room 2.

As shown in FIG. 1, in the operation room 2, there are a patient bed 10 on which a patient 48 lies and an endoscopic operation system 1 mounted on a cart 11 placed inside.

The cart 11 has medical instruments as controlled apparatuses placed thereon, such as the apparatus including an electric knife apparatus 13, an aeroperitoneum apparatus 14, an endoscopic camera apparatus 15, a light source apparatus 16 and a video tape recorder (VTR) 17 and a compressed gas cylinder 18 filled up with carbon dioxide or the like. The endoscopic camera apparatus 15 is connected to a first endoscope 31 via a camera cable 31a. The light source apparatus 16 is connected to the first endoscope 31 via a light guide cable 31b.

The cart 11 also has a display unit 19, a first centralized display panel 20, an operation panel 21 which is a touch panel controller and the like placed thereon. The display unit 19 is a TV monitor for instance, which displays an endoscopic image and the like.

The centralized display panel 20 is display means capable of selectively displaying any data during an operation. The operation panel 21 is a centralized operating apparatus composed of a display such as a liquid crystal display and a touch panel, for instance, integrally provided on the display, which is operated by a nurse or the like who is in a non-sterilization area.

The cart 11 further has a system controller 22 placed thereon. The system controller 22 is connected to the above-mentioned electric knife apparatus 13, aeroperitoneum apparatus 14, endoscopic camera apparatus 15, light source apparatus 16 and VTR 17 via a communication wire not shown.

The system controller 22 is connectable to a headset-type microphone 33. The system controller 22 can recognize voice inputted from the microphone 33 and control each of the instruments according to the voice of an operator.

In the case where communication is being performed between the system controller 22 and these apparatuses, the system controller 22 can display a setting screen of a setup state and operating switches and the like of the connected apparatuses on the liquid crystal display of the above-mentioned operation panel 21. The system controller 22 further allows a manipulated input such as a change of a set value by touching a desired operating switch of the operation panel 21 and operating the touch panel of a predetermined area.

A remote controller 30 is a second centralized operating apparatus to be operated by a surgeon or the like who is in a sterilization area, which can operate the other apparatus in established communication via the system controller 22.

The system controller 22 is connected to a patient monitor system not shown, and is capable of analyzing biologic information obtained from the patient monitor system and displaying the analysis result on a required display unit as will be described later.

The system controller 22 also has an infrared communication port (not shown) as communication means mounted thereon. The infrared communication port is provided in a position where an infrared ray is easily radiated such as proximity of the display unit 19, and is connected with the system controller 22 by a cable. The system controller 22 is connected via a network cable 9 to an in-house server not shown by an in-house LAN.

As shown in FIG. 2, the electric knife apparatus 13 drives an electric knife probe 13a by a power supply circuit 130 and a high-frequency generation circuit 131 and treats an affected area based on control of a control circuit 140. An output status (operational status) of the high-frequency generation circuit 131 is fed back to the control circuit 140 as operational status detection means by an A/D converter 134.

The electric knife probe 13a is provided with an RF-ID chip 13b storing a probe ID which is a type of the electric knife probe 13a. The electric knife apparatus 13 is configured to be capable of exchanging data with the RF-ID chip 13b by using an RF-ID antenna section 135 and sending and receiving the probe ID via an RF-ID W/R circuit 136.

Furthermore, the control circuit 140 of the electric knife apparatus 13 drives the electric knife probe 13a with a foot manipulate signal of a foot SW 40 (refer to FIG. 1) as a trigger signal. The control circuit 140 also samples and takes in an output voltage and an output current of the high-frequency generation circuit 131 at a predetermined timing interval (every 50 ms for instance) with the foot manipulate signal of the foot SW 40 as a trigger signal so as to calculate output power and impedance from the output voltage or the output current taken in. And the control circuit 140 stores the output voltage, output current, output power and impedance in a log memory 138 as treatment instrument operational status recording means. Furthermore, the control circuit 140 is configured to be capable of sending and receiving various data to and from the system controller 22 via a communication interface (hereinafter, described as communication I/F) circuit 137. The control circuit 140 stores the probe ID obtained via the RF-ID W/R circuit 136 in the log memory 138.

As shown in FIG. 3, the endoscopic camera apparatus 15 includes a CCD driver 160 for driving a CCD (not shown) as an image pickup device of the endoscope 31 and a preprocessing circuit 161 for performing preprocessing (correlated double sampling process, A/D conversion and the like) to an image pickup signal from the CCD (not shown) for instance. The image pickup device of the endoscope 31 is not limited to the CCD but may also be composed of a C-MOS sensor.

The endoscopic camera apparatus 15 also includes a video signal processing circuit 162 for signal-processing a video signal digitalized from the image pickup signal by the pre-processing circuit 161 and a video output circuit 163 for outputting the video signal signal-processed by the video signal processing circuit 162 to the display unit 19.

The endoscopic camera apparatus 15 further includes a frame memory section 164 for recording the video signal signal-processed by the video signal processing circuit 162 as a current frame image for 5 seconds for instance and an image storage section 165 for storing a frame image recorded in the frame memory section 164 for at least 3 seconds for instance before and after generation time of the trigger signal in predetermined timing with the foot manipulate signal of the foot SW 40 (refer to FIG. 1) as the trigger signal.

The endoscopic camera apparatus 15 also includes a control circuit 170 for controlling each of the sections, where the control circuit 170 is configured to be capable of sending and receiving various data to and from the system controller 22 via a communication I/F circuit 166.

Timing of image storage in the image storage section 165 is controlled by the control circuit 170. For more details, the control circuit 170 inputs the foot manipulate signal of the foot SW 40 (refer to FIG. 1) (detected by the control circuit 140 as the operational status detection means) as the trigger signal via the system controller 22 so as to control timing of storing the frame image of the frame memory section 164 in the image storage section 165.

As shown in FIG. 4, the system controller 22 comprises communication I/F circuit 220 for sending and receiving the data to and from the electric knife apparatus 13, the aeroperitoneum apparatus 14, the endoscopic camera apparatus 15, the light source apparatus 16 as the medical instruments which are controlled apparatuses for instance, and a system control circuit 221 for controlling these medical instruments which are the controlled apparatuses via the communication I/F circuit 220.

The system control circuit 221 comprises a peripheral apparatus control section 222, a treatment instrument output data analysis section 223, an operation panel control section 224, a centralized display control section 225 and a network control section 226.

The peripheral apparatus control section 222 is the control section for sending and receiving the data to and from the electric knife apparatus 13, the aeroperitoneum apparatus 14, the endoscopic camera apparatus 15 and the light source apparatus 16 for instance as the medical instruments which are the controlled apparatuses via the communication I/F circuit 220 so as to control each of the apparatuses.

The operation panel control section 224 is the control section for sending and receiving the data to and from the operation panel 21 so as to control the operation panel 21.

The centralized display control section 225 is the control section for controlling the centralized display panel 20.

The network control section 226 is the control section for executing an in-house LAN connection process via the network cable 9 (refer to FIG. 1).

The treatment instrument output data analysis section 223 is an analysis section for analyzing output data of the electric knife probe 13*a* (refer to FIG. 2) connected to the electric knife apparatus.

As shown in FIG. 5, the treatment instrument output data analysis section 223 includes a probe ID extraction section 250 as treatment instrument type identifying means for extracting a probe ID of the electric knife probe 13*a* out of electric knife data from the electric knife apparatus 13. The treatment instrument output data analysis section 223 also includes an output waveform extraction section 251 for extracting output waveform data on the electric knife probe 13*a* out of the electric knife data from the electric knife apparatus 13.

The treatment instrument output data analysis section 223 further includes a data analysis section 252 as operational status analysis means for analyzing the output waveform data on the electric knife probe 13*a* extracted by the output waveform extraction section 251 and handling information extraction means, an endoscopic image storage section 253 for storing an endoscopic image from the image storage section 165, and an analysis result output section 255 as notification means for displaying an analysis result analyzed by the data analysis section 252 on the centralized display panel 20.

The endoscopic image storage section 253 is an image data storage section for reading out and storing endoscopic image data (endoscopic camera apparatus data) from the image storage section 165 of the endoscopic camera apparatus 15 when the output waveform data on the electric knife probe 13*a* analyzed by the data analysis section 252 is outputted.

The analysis result output section 255 of the treatment instrument output data analysis section 223 can display a synthesized synthetic image of the frame image stored by the image storage section 165 of the endoscopic camera apparatus 15 and stored in the endoscopic image storage section 253 and the analysis result analyzed by the data analysis section 252 on the centralized display panel 20.

The data analysis section 252 of the treatment instrument output data analysis section 223 analyzes the output waveform data on the electric knife probe 13*a* extracted by the output waveform extraction section 251 based on model waveforms and corresponding information stored in a model waveform storage section 254*a* and a corresponding information storage section 254*b* as handling information storage means.

A description will be given later as to the model waveforms stored in the model waveform storage section 254*a* and the corresponding information stored in the corresponding information storage section 254*b*.

Next, operations of the present embodiment thus configured will be described by using the flowchart of FIG. 6 and the explanatory diagrams of FIGS. 7 to 17.

First, if the power of the system controller 22 and the electric knife apparatus 13 is turned on, internal time of the electric knife apparatus 13 is matched to the internal time of the system controller 22.

As shown in FIG. 6, if a procedure by the endoscopic operation system 1 is started in a step S1, the probe ID is detected by the electric knife apparatus 13 via the RF-ID W/R circuit 136 so as to store the obtained probe ID in the log memory 138 (treatment instrument identification information detecting step).

And in a step S2, the endoscopic operation system 1 determines whether or not there has been a treatment output instruction signal (foot manipulate signal of the foot SW 40) in the electric knife apparatus 13 (operational status detection step).

If there is the treatment output instruction signal, the endoscopic operation system 1 starts a treatment output in the electric knife apparatus 13 with the treatment output instruction signal as the trigger signal in a step S3.

Subsequently, the endoscopic operation system 1 samples the output data in the electric knife apparatus 13 via the A/D converter 134 with the treatment output instruction signal as the trigger signal in a step S4, and also stores the sampled output waveform data in the log memory 138 (treatment instrument operational status recording step).

As shown in FIG. 7, the output data is composed of voltage data and current data sampled at 50-ms intervals for instance.

Furthermore, the endoscopic operation system 1 stores multiple frame images 500a taken for at least a few seconds before and after as shown in FIG. 8 in the image storage section 165 with the treatment output instruction signal as the trigger signal in a step S5, the frame images 500a recorded in the frame memory section 164 of the endoscopic camera apparatus 15.

And the endoscopic operation system 1 waits for an analysis instruction/order from the operation panel 21 in a step S6. If there is no analysis instruction/order, it returns to the step S2. If there is the analysis instruction/order, it moves on to a step S7.

The analysis instruction/order is an order issued by the operator in the case where a desired treatment result cannot be obtained when the operator implements the treatment with the electric knife apparatus 13. A waveform analysis described later is performed according to the order, and an analysis result is displayed on the centralized display panel 20. The operator can accurately grasp the current treatment in the electric knife apparatus 13 by checking the analysis result on the centralized display panel 20.

In the step S7, the endoscopic operation system 1 performs the waveform analysis based on the probe ID stored in the log memory 138 and the sampled output waveform data (operational status analysis step).

To be more precise, as shown in FIG. 9, the output waveform data on the electric knife probe 13a extracted by the output waveform extraction section 251 is analyzed based on the model waveforms and corresponding information of each probe ID stored in the model waveform storage section 254a and the corresponding information storage section 254b of a database section 254. For instance, in the case of Probe ID=i, Model waveform=Output pattern Pj, then correspondence (i, j) which is the corresponding information is the analysis result. Although not shown, the correspondence (i, j) is linked to corresponding comment information stored in the database section 254, and the endoscopic operation system 1 extracts the corresponding comment information from the database section 254 (handling information extraction step).

And as shown in FIG. 10, the endoscopic operation system 1 displays output waveform data 502 and frame images 500 as the analysis result together with the corresponding comment information 504 on the centralized display panel 20 in a step S8 (operational status notifying step).

The corresponding comment information is handling information extracted from the database section 254 as the handling information storage means when analyzing the output waveform data as the operational status of a treatment instrument, the data sampled and stored in the log memory 138 as treatment instrument operational status recording means.

The endoscopic operation system 1 repeats the process until it detects the end of the procedure in a step S9.

FIG. 10 shows a display example of the centralized display panel 20 when displaying the corresponding comment information 504 with the output waveform data 502 and frame images 500 in the case where the probe ID is 01 (monopolar hook electrode or knife electrode) and the output waveform data is model pattern=01. In the case of FIG. 10, the treatment condition is determined to be the state in which "discharge is occurring from the electric knife probe 13a, and the electrode is larger than a set value (the set value is smaller)" or the state in which "the electrode is sinking in saline/blood." It displays a comment of "increase the set value" or "suck the liquid around the electrode" as the corresponding comment information 504 so as to prompt the operator to react.

FIG. 11 shows a display example of the centralized display panel 20 when displaying the corresponding comment information 504 with the output waveform data 502 and frame images 500 in the case where the probe ID is 02 (monopolar snare electrode) and the output waveform data is model pattern=01. In the case of FIG. 11, the treatment condition is determined to be the state in which "discharge is not occurring, but squeezing the snare" or the state in which "bleeding from a polyp scar." It displays a comment of "increase the set value" or "do not squeeze the snare until the discharge can be confirmed" as the corresponding comment information 504 so as to prompt the operator to react.

FIG. 12 shows a display example of the centralized display panel 20 when displaying the corresponding comment information 504 with the output waveform data 502 and frame images 500 in the case where the probe ID is 03 (monopolar loop electrode) and the output waveform data is model pattern=02. In the case of FIG. 12, the treatment condition is determined to be the state in which "discharge is occurring and bleeding is stopped, but bleeding again if the electrode is moved." It displays a comment of "do not move the electrode" or "decrease the set value or use a weak discharge mode" as the corresponding comment information 504 so as to prompt the operator to react.

FIG. 13 shows a display example of the centralized display panel 20 when displaying the corresponding comment information 504 with the output waveform data 502 and frame images 500 in the case where the probe ID is 01 (monopolar hook electrode or knife electrode) and the output waveform data is model pattern=03. In the case of FIG. 13, the treatment condition is determined to be the state in which "outputted by pressing the electrode against the tissue" or the state in which "bleeding or the tissue adhering to the electrode when the electrode is pulled." It displays a comment of "increase the set value or use a strong discharge mode" or "use a noncontact coagulation mode" as the corresponding comment information 504 so as to prompt the operator to react.

FIG. 14 shows a display example of the centralized display panel 20 when displaying the corresponding comment information 504 with the output waveform data 502 and frame images 500 in the case where the probe ID is 01 (monopolar hook electrode or knife electrode) and the output waveform data is model pattern=04. In the case of FIG. 14, the treatment condition is determined to be the state in which "the discharge and tissue degeneration cannot be confirmed." It displays a comment of "confirm by contact or replace the A cord" or "replace the accessory" as the corresponding comment information 504 so as to prompt the operator to react.

FIG. 15 shows a display example of the centralized display panel 20 when displaying the corresponding comment information 504 with the output waveform data 502 and frame images 500 in the case where the probe ID is 11 (bipolar forceps electrode) and the output waveform data is model pattern=11. In the case of FIG. 15, the treatment condition is determined to be the state in which "the electrode is larger with respect to the set value (the set value is smaller)" or the state in which "the electrode is sinking in saline/blood." It displays a comment of "increase the set value" or "suck the liquid around the electrode" as the corresponding comment information 504 so as to prompt the operator to react.

FIG. 16 shows a display example of the centralized display panel 20 when displaying the corresponding comment information 504 with the output waveform data 502 and frame images 500 in the case where the probe ID is 11 (bipolar forceps electrode) and the output waveform data is model pattern=12. In the case of FIG. 16, the treatment condition is determined to be the state in which "the output is noncharacteristic." It displays a comment of "increase the set value" or "suck the liquid around the electrode" as the corresponding comment information 504 so as to prompt the operator to react.

FIG. 17 shows a display example of the centralized display panel 20 when displaying the corresponding comment information 504 with the output waveform data 502 and frame images 500 in the case where the probe ID is 11 (bipolar forceps electrode) and the output waveform data is model pattern=13. In the case of FIG. 17, the treatment condition is determined to be the state in which "the electrode has a scorched tissue thereon." It displays a comment of "clean the electrode" or "output while supplying water" as the corresponding comment information 504 so as to prompt the operator to react.

Thus, according to the present embodiment, a detailed analysis can be made as to a control state of the medical instrument during the procedure. And the operator is notified of the analysis result on the centralized display panel 20 so that the operator can accurately grasp the current treatment in the electric knife apparatus 13.

Second Embodiment

Figures 18, 19:
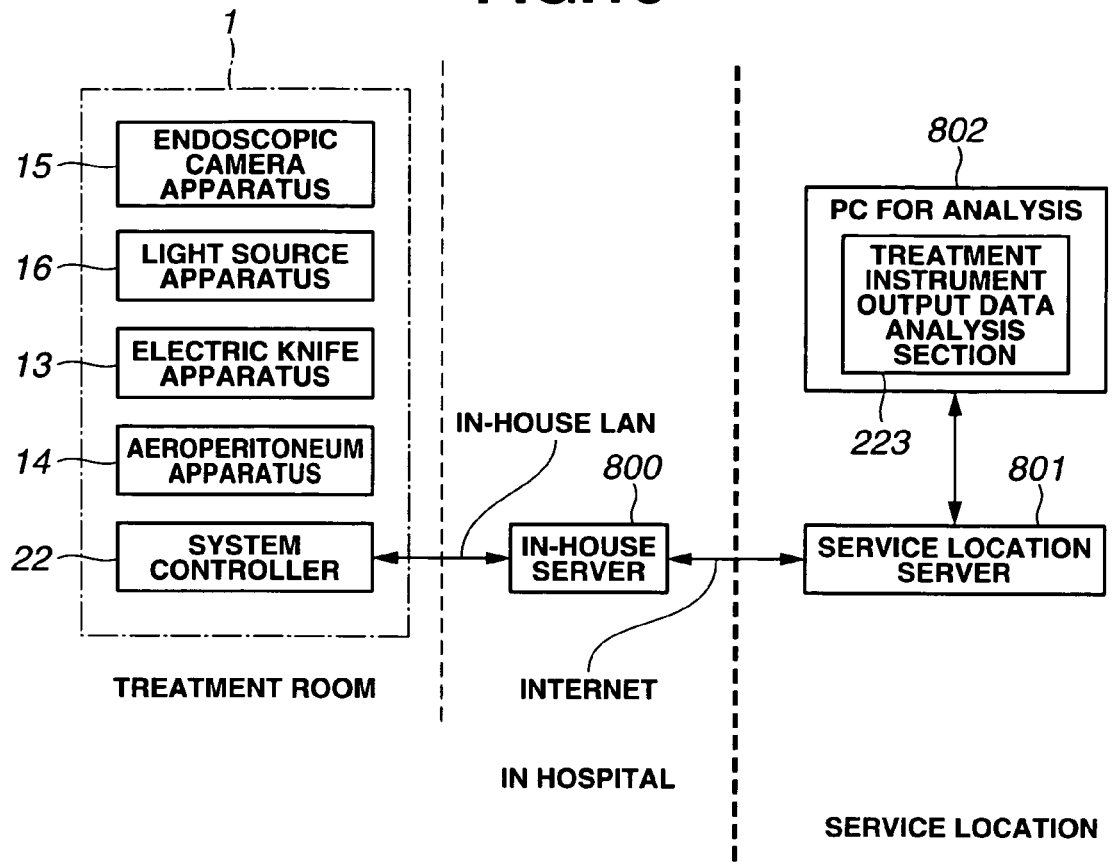
FIG. 18 is a block diagram showing the configuration of the endoscopic operation system according to a second embodiment of the present invention.
FIG. 19 is an explanatory diagram describing workings of the endoscopic operation system of FIG. 18.

FIGS. 18 and 19 relate to a second embodiment of the present invention. FIG. 18 is a block diagram showing the configuration of the endoscopic operation system. FIG. 19 is an explanatory diagram describing the workings of the endoscopic operation system of FIG. 18.

As the second embodiment is almost the same as the first embodiment, only the differences will be described. The same configurations as the first embodiment will be given the same symbols, and a description thereof will be omitted.

According to the present embodiment, as shown in FIG. 18, the treatment instrument output data analysis section 223 provided in the system controller 22 in the first embodiment is provided in an external PC for analysis 802.

The PC for analysis 802 is connected to the system controller 22 via an in-house server 800 connected to the in-house LAN and a service location server 801 set up in a service center of a manufacturer or the like. The internal time of the system controller 22 is matched to the internal time of the service location server 801. The other configurations are the same as the first embodiment.

According to the present embodiment thus configured, the output waveform data and a scope ID are outputted to the PC for analysis 802 via the system controller 22 after the operation. The PC for analysis 802 analyzes the output waveform data on the electric knife probe 13a based on the model waveforms and corresponding information.

In general, use of the electric knife apparatus 13 requires a considerable level of technique of the operator so that improvement in the technique of the operator is one of the issues in doctor education. Therefore, it is desired nowadays to set up indexes which quantify technical levels for the sake of guidance at educational institutions such as university hospitals or individual study.

To solve the problem, an object of the present embodiment is to set up the indexes by statistically processing the usage status of the electric knife apparatus 13 with the external PC for analysis 802.

In the case of a TUR operation for instance, the usage status of the electric knife apparatus 13 is as indicated in the following (1) to (5) depending on skills of the operator (refer to FIG. 19).

(1) Number of Times of Dissection/Total Number of Times of Output (=Dissection Time/Total Output Time)

An expert only performs minimum necessary stop of bleeding=coagulation. As a result of this, an inexperienced operator is apt to perform more than necessary stop of bleeding=coagulation. Therefore, if the number of times of dissection/total number of times of output is compared between a high skill level of the operator and a low skill level of the operator, the following holds. Number of times of dissection/total number of times of output (high skill level) <number of times of dissection/total number of times of output (low skill level)

(2) Average Dissection Time

An inexperienced operator is apt to stop output after a short time, fearing perforation and the like. Therefore, if the average dissection time is compared between the high skill level of the operator and the low skill level of the operator, the following holds. Average dissection time (high skill level) >average dissection time (low skill level)

(3) Average Coagulation Time

An inexperienced operator is apt to output for a long time before bleeding is stopped and thereby coagulate a large portion for reasons such as being unsure about a bleeding point and not knowing an effective method of stopping bleeding. Therefore, if the average coagulation time is compared between the high skill level of the operator and the low skill level of the operator, the following holds. Average coagulation time (high skill level)<average coagulation time (low skill level)

(4) Dissection Time/Operation Time

An inexperienced operator is apt to waste time by hesitating to perform a treatment before bleeding. Therefore, if the dissection time/operation time is compared between the high skill level of the operator and the low skill level of the operator, the following holds. Dissection time/operation time (high skill level)<dissection time/operation time (low skill level)

(5) Excision Volume/Dissection Time

An inexperienced operator is apt to avoid cutting deeply into the tissue, fearing perforation and the like. Therefore, if the excision volume/dissection time is compared between the high skill level of the operator and the low skill level of the operator, the following holds. Excision volume/dissection time (high skill level)>excision volume/dissection time (low skill level)

According to the present embodiment, the PC for analysis 802 calculates the indexes (1) to (5) and stores them in a call ready state for each individual case. The PC for analysis 802 also calculates averages of the indexes for a period of three months or so as to each individual operator and case type and stores them in a call ready state.

According to the present embodiment, the operator can access the service location server 801 and browse a list of the indexes of the operator to which access is allowed by the PC for analysis 802. For instance, the operator in a guiding position can check index data on all the doctors to be guided and use the index data as a referenced for a guiding principle.

As for the case requiring a high output such as the TUR operation, the operator estimated applied energy from an impression of output time and power setup of the apparatus according to the operator's own memory. According to the present embodiment, however, it is possible to quantitatively grasp the applied energy. A detailed description will be given below.

Electric energy can be acquired as a product of output power and time. To be more specific, total applied energy is an integration value wherein (output power measured by the apparatus)×(measurement interval) is measured as to one case.

Thus, the PC for analysis 802 integrates (output power measured by the apparatus)×(measurement interval=50 ms) as to one case, and stores it in the call ready state. Therefore, the operator can quantitatively grasp the applied energy with ease by accessing the PC for analysis 802.

Third Embodiment

Figure 20:
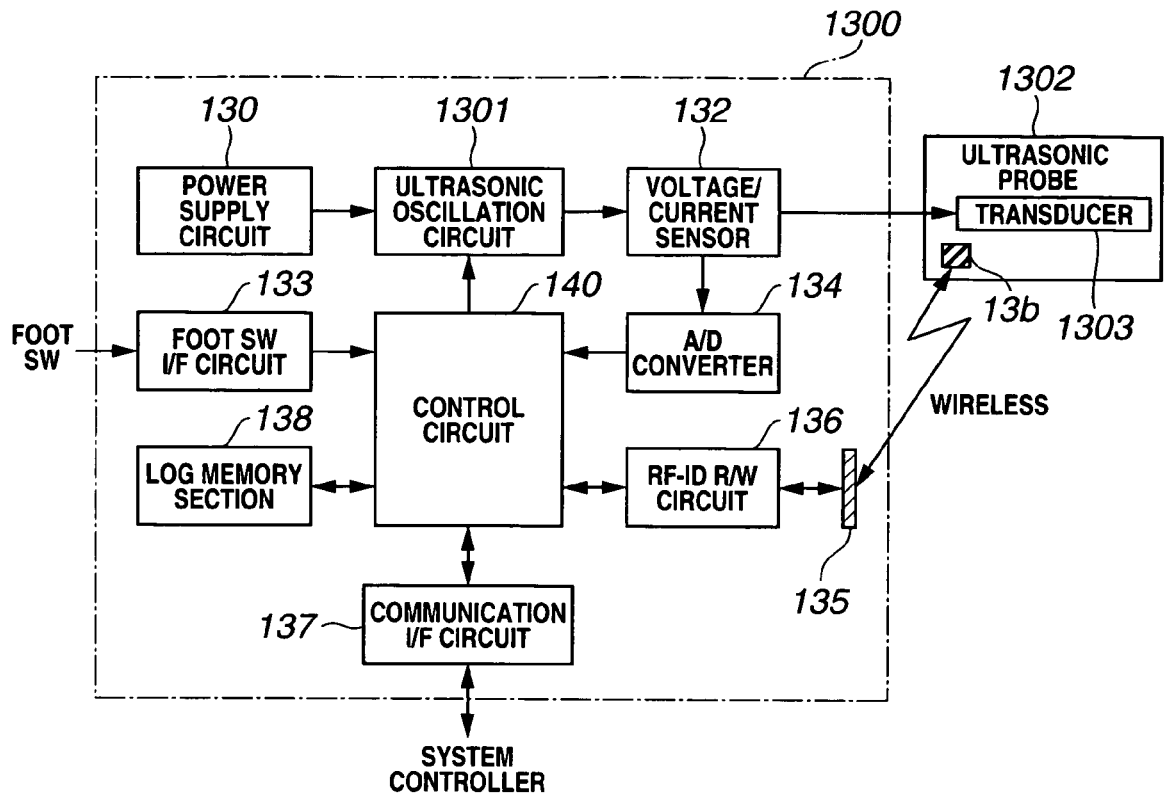
FIG. 20 is a block diagram showing the configuration of the endoscopic operation system according to a third embodiment of the present invention.
Figure 21:
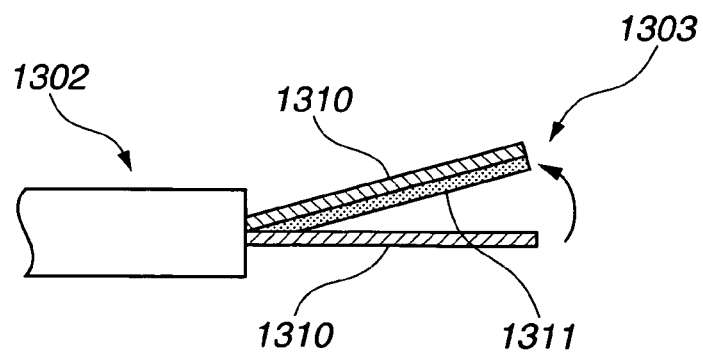
FIG. 21 is a drawing showing the configuration of a distal end of an ultrasonic probe of FIG. 20.
Figure 22:
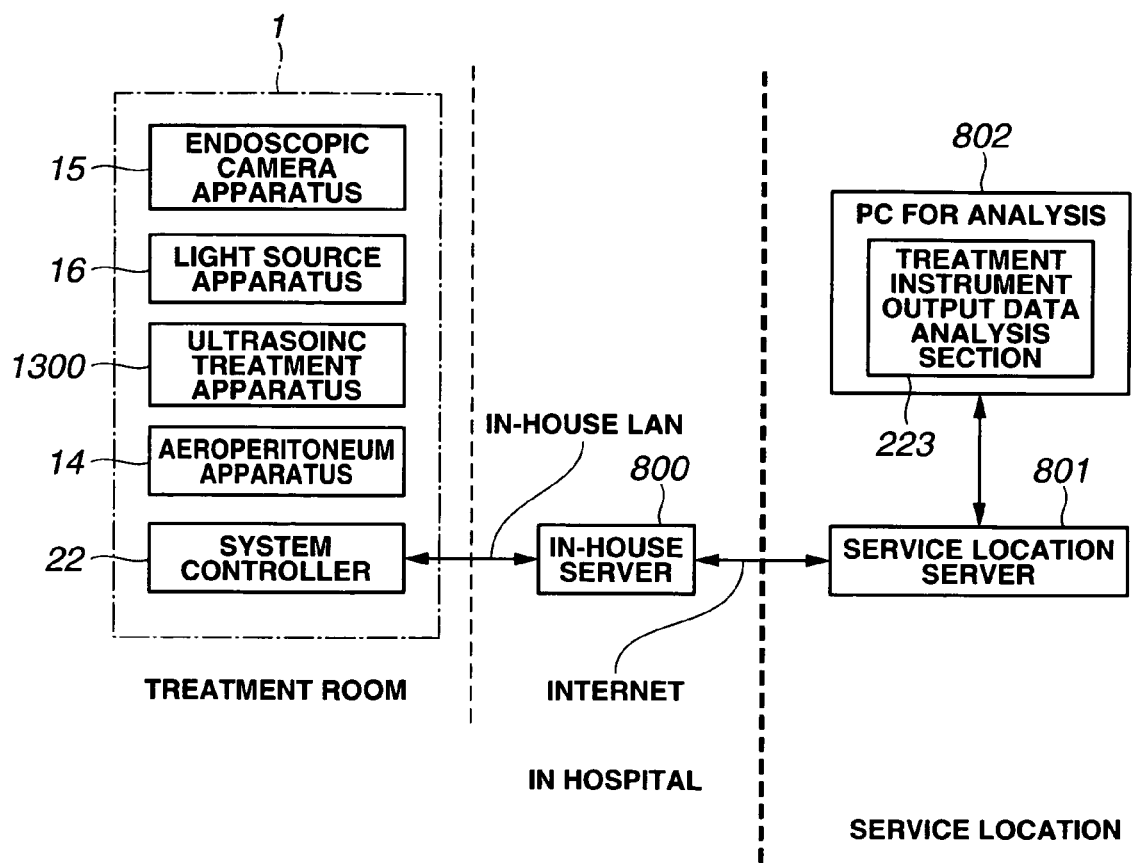
FIG. 22 is a block diagram showing the configuration of a variation of the endoscopic operation system of FIG. 20.

FIGS. 20 to 22 relate to a third embodiment of the present invention. FIG. 20 is a block diagram showing the configuration of the endoscopic operation system. FIG. 21 is a drawing showing the configuration of a distal end of an ultrasonic probe of FIG. 20. FIG. 22 is a block diagram showing the configuration of a variation of the endoscopic operation system of FIG. 20.

As the third embodiment is almost the same as the first embodiment, only the differences will be described. The same configurations as the first embodiment will be given the same symbols, and a description thereof will be omitted.

According to the present embodiment, as shown in FIG. 20, the endoscopic operation system 1 is configured by using an ultrasonic treatment apparatus (ultrasonic dissection and coagulation apparatus) 1300 instead of the electric knife apparatus 13.

An ultrasonic probe 1302 of the ultrasonic treatment apparatus (ultrasonic dissection and coagulation apparatus) 1300 is configured by including an ultrasonic transducer 1303 at its distal end. The other configurations are the same as the first embodiment.

If outputted with a metal component such as a clip sandwiched, the ultrasonic probe 1302 may have a crack in the gripped portion so that the distal end of the probe can be broken or dropped by subsequent use.

The ultrasonic probe 1302 is driven at a constant current, and so an ultrasonic output becomes larger with the metal component such as a clip sandwiched than with the tissue such as a blood vessel or an intestinal membrane sandwiched. On the other hand, even with hard tissue such as a ligament sandwiched, the ultrasonic output becomes larger than with the tissue such as a blood vessel or an intestinal membrane sandwiched. In the state, however, the gripped portion will not have a crack therein.

According to the present embodiment, in the case where the ultrasonic output is larger than a predetermined value, it is possible to display the endoscopic image on the centralized display panel 20 and determine whether or not the metal component such as a clip is sandwiched according to the endoscopic image.

As described above, at the gripping portion provided at the distal end of the ultrasonic probe 1302, if the metal component such as a clip is directly pressed against a metal site 1310 performing ultrasonic vibration, a crack may be generated or a harsh-sounding high sound is generated. Thus, as shown in FIG. 21, a resin 1311 may be provided to the gripping portion between the metal sites 1310. However, such a resin 1311 wears each time the output is performed. Therefore, limit of use of the resin 1311 is 20 times or so for instance, and it needs to be replaced thereafter.

According to the present embodiment, output information (output set value, distal end serial number) of the ultrasonic probe 1302 is stored in the log memory 138 (refer to FIG. 20). The treatment instrument output data analysis section 223 integrates the output information, and notifies the centralized display panel 20 of replacement of the end of the ultrasonic probe 1302 at a time point of 80% of estimated usable time based on the integrated output information.

As shown in FIG. 22, it is possible, according to the present embodiment, to provide the treatment instrument output data analysis section 223 placed in the system controller 22 in the external PC for analysis 802 as in the second embodiment.

As above, it is possible, according to each of the above-described embodiments, to provide the operation system capable of analyzing a treatment status including organization information and a method of notifying system operation information thereof.

The treatment status includes at least all of the treatment status, usage of the treatment instrument and control status of the medical instrument.

The present invention is not limited to the above-mentioned embodiments, but various changes, modifications and the like may be made without departing from the scope of the invention.

What is claimed is:

1. An operation system comprising:
    a treatment instrument used for a medical treatment apparatus for performing a treatment on an affected area;
    operational status detection means for detecting operational status of the treatment instrument;
    treatment instrument operational status recording means for recording the operational status of the treatment instrument detected by the operational status detection means;
    operational status analysis means for analyzing the operational status of the treatment instrument recorded by the treatment instrument operational status recording means;
    handling information storage means in which handling information differing for each analysis result is linked and stored, said handling information obtained by analyzing the operational status of the treatment instrument by the operational status analysis means; and
    handling information extraction means for extracting the handling information stored in the handling information storage means based on the operational status of the treatment instrument analyzed by the operational status analysis means.

2. The operation system according to claim 1, further comprising:
    treatment instrument type identifying means for identifying a type of the treatment instrument, and wherein:
    the handling information storage means links and stores the handling information differing for the each analysis result obtained by analyzing the operational status of the treatment instrument as to each type of the treatment instrument; and
    the operational status analysis means analyzes the operational status of the treatment instrument recorded by the treatment instrument operational status recording means based on the type of the treatment instrument.

3. The operation system according to claim 1, wherein:
    the operational status detection means samples the operational status of the treatment instrument for each use of the treatment instrument at sampling intervals in predetermined timing so as to detect the statuses as multiple pieces of sampling information.

4. The operation system according to claim 1, further comprising:
    notification means for notifying an analysis result of the operational status analysis means.

5. The operation system according to claim 1, wherein:
the operational slams analysis means is connected to the handling information extraction means and the treatment instrument operational status recording means via a communication line.

6. The operation system according to claim 1, wherein:
at least the handling information storage means, the operational status analysis means and the handling information extraction means are provided in an external apparatus network-connected with the handling information storage means, the operational status detection means and the treatment instrument operational status recording means; and
the handling information extraction means extracts statistic handling information which is usage results of the treatment instrument in the medical treatment apparatus statistically processed based on the handling information stored in the handling information storage means and the operational status of the treatment instrument analyzed by the operational status analysis means.

7. A method of notifying system operation information of an operation system comprising:
a treatment instrument identification information detecting step of detecting identification information for identifying a type of a treatment instrument used for a medical treatment apparatus for performing a treatment on an affected area;
an operational status detection step of detecting operational status information of the treatment instrument;
a treatment instrument operational status recording step of recording the operational status information of the treatment instrument detected by the operational status detection step;
an operational status analysis step of analyzing the operational status information of the treatment instrument recorded by the treatment instrument operational status recording step based on the identification information detected by the treatment instrument identification information detecting step;
a handling information extraction step of extracting the handling information based on the operational status information of the treatment instrument analyzed by the operational status analysis step from the handling information storage means in which the handling information differing for each analyses result obtained by the operational status analysis step analyzing the operational status information for each type of the treatment instrument is linked and stored; and
an operational status notifying step of outputting the operational status information analyzed by the operational status analysis step to notification means based on a predetermined notification condition.

* * * * *